United States Patent [19]

Traeger et al.

[11] 4,151,349

[45] Apr. 24, 1979

[54] CRYSTALLINE POTASSIUM SALT OF β-NICOTINAMIDE ADENINE DINUCLEOTIDE PHOSPHORIC ACID AND METHOD FOR ITS PREPARATION

[75] Inventors: Heinrich Traeger, Penzberg; Herbert Brustmann; Erich Haid, both of Tutzing, all of Fed. Rep. of Germany

[73] Assignee: Boehringer Mannheim GmbH, Mannheim-Waldhof, Fed. Rep. of Germany

[21] Appl. No.: 836,112

[22] Filed: Sep. 23, 1977

[30] Foreign Application Priority Data

Feb. 1, 1977 [DE]   Fed. Rep. of Germany ....... 2704109

[51] Int. Cl.$^2$ ...................... C07H 17/00; A61K 31/70
[52] U.S. Cl. ........................................ 536/28; 536/29; 424/180; 536/27
[58] Field of Search .................................. 536/27, 28

[56] References Cited

U.S. PATENT DOCUMENTS 3,413,283   11/1968   Nomura et al. ...................... 536/27

FOREIGN PATENT DOCUMENTS 930428   8/1961   United Kingdom ...................... 536/27
1197758   7/1970   United Kingdom ...................... 536/27

*Primary Examiner*—Johnnie R. Brown
*Assistant Examiner*—Blondel Hazel
*Attorney, Agent, or Firm*—Sprung, Felfe, Horne, Lynch & Kramer

[57] ABSTRACT

The invention provides a novel crystalline potassium salt of β-nicotinamide adenine dinucleotide phosphoric acid (β-NADP-K), having a primitively orthorhombic crystal system, which salt is more pure and more stable than the conventional amorphous form, and is advantageously not hygroscopic. The novel salt is produced by treating a dilute aqueous solution of the potassium salt of β-nicotinamide adenine dinucleotide phosphoric acid with a hydrophilic water soluble organic solvent at a pH value of 2 to 5 until turbidity sets in, permitting crystallization and then separating the crystals.

1 Claim, No Drawings

CRYSTALLINE POTASSIUM SALT OF β-NICOTINAMIDE ADENINE DINUCLEOTIDE PHOSPHORIC ACID AND METHOD FOR ITS PREPARATION

The invention relates to a novel crystalline potassium salt of β-nicotinamide adenine dinucleotide phosphoric acid and a method for its preparation.

β-Nicotinamide adenine dinucleotide phosphoric acid, hereinafter β-NADP, has an important function in biological oxidation procedures as a coenzyme of many dehydrogenases. Also, β-NADP plays an especially important role in the synthesis of fatty acids.

In recent times, β-NADP has been gaining importance chiefly as a measurement parameter in enzymatic analysis in the determination of enzyme activities and substrate concentrations for clinical diagnosis, while at the same time the requirements with regard to the purity, stability and freedom from inhibitor of this product have become increasingly stringent. The industrial production of NADP has accordingly become more and more complex.

In all known methods of preparing NADP, the final stage provides a solution of the sodium salt which is brought into solid form by methods such as precipitation with organic solvents, spray drying and/or freeze drying. The impurities still present in this solution, such as adenosine-5-monophosphate (AMP), β-nicotinamide adenine dinucleotide (β-NAD) and 2'-phosphoadenosine-5'-diphosphoribose (2 P-ADP-ribose) and dehydrogenase inhibitors have not been able to be further separated by the subsequent steps of the process.

The β-NADP-Na obtained by one of the known methods is amorphous, hygroscopic, and deliquescent. This instability of the amorphous β-NADP-Na therefore requires special, usually cost-increasing precautions (exclusion of air, protective gas and the like) in storage, shipment and processing.

The present invention provides a salt of β-nicotinamide adenine dinucleotide phosphoric acid which does not have the above-described disadvantages, viz., a crystalline potassium salt of β-NADP.

The crystalline NADP potassium salt of the invention has the following crystallographic characteristics:
Crystal system: Primitively orthorhombic
Space group: $P2_1 2_1 2_1$ or $P2_1 2_1 2$
Cell dimensions: $a = 52.23 \text{ Å} \pm 0.04$
$b = 16.89 \text{ Å} \pm 0.03$
$c = 8.45 \text{ Å} \pm 0.03$ The crystalline NADP-K is considerably more pure, more free from inhibitor, and more stable than the amorphous product known heretofore, and it has the great advantage that it is not hygroscopic.

In further aspect, the invention provides a process for preparing this crystalline potassium salt of β-NADP. This process comprises converting β-nicotinamide adenine dinucleotide phosphoric acid (in the form of its free acid or of one of its salts) to dilute aqueous solution of the potassium salt, and treating same, at a pH value of 2 to 5, preferably 3.0, with a hydrophilic, water-soluble organic solvent until turbidity sets in, stirring until crystallization of NADP-K begins, and then separating the crystals. The stirring of the solution can be omitted, but the residual crystallization of NADP-K then will take longer.

It is preferable to use methanol as the hydrophilic organic solvent, with an NADP-K solution-to-solvent ratio of 1:0.5 to 4, a ratio of from 1:1.0 to 1.5 being especially preferred; to operate at constant temperature, preferably room temperature, until the onset of crystallization, and then to lower the temperature to, say $-10°$ C., preferably to 0° to $+4°$ C., for the complete crystallization of NADP-K.

In general, the aqueous NADP-K solution has, prior to the crystallization, a concentration of 2 to 35%, preferably 7 to 10%.

Additional examples of suitable hydrophilic solvents are alkanols, such as ethanol and propanol, ethers such as dioxane, and low ketones such as acetone, and mixtures thereof.

These hydrophilic organic solvents must be sufficiently miscible in water, so that a homogeneous water-solvent system can be obtained for the crystallization of NADP-K.

The time required for the crystallization depends on the nature and amount of the impurities present in the solution, on the nature of the water-soluble organic solvents, and on the temperature and other such factors. The crystallization is usually substantially completed within 2 to 48 hours after the beginning of crystallization. The addition of seed crystals to accelerate crystallization is advantageous, especially when large amounts of impurities are present in the aqueous NADP-K solution, such as AMP and NAD.

The invention creates crystalline β-NADP-K and a method for the simple technical production thereof, the new substance being characterized, in contradistinction to the β-NADP-Na prepared by the formerly conventional, espensive precipitation methods, by higher purity, freedom from inhibitor, better stability, and the absence of hygroscopicity.

The following examples illustrate the invention:

EXAMPLE 1

10 g of amorphous β-NADP-Na$_2$ is dissolved in 30 ml of desalted H$_2$O, transformed to the free acid by means of an ion exchanger (Dowex 50, Amberlite IR 120) and adjusted with dilute KOH to a pH of 3.0. After dilution of the solution to 115 ml (β-NADP concentration = 7.5%), approximately 115 ml of methanol is added at room temperature, with stirring (the solution becomes slightly turbid). After about 30 minutes the crystallization of β-NADP-K begins. After the further addition of 55 ml of methanol, the mixture is placed, without stirring, in the refrigerator ($+4°$ C.) for the residual crystallization of β-NADP-K. After about 20 hours, the crystallizate is suction filtered, washed with acetone, and dried in vacuo without drying agent.

The yield amounts to about 9.2 g of β-NADP-K (92% of the theory).

EXAMPLE 2

Approximately 100 ml of acetone is added, with stirring, to 100 ml of a 6% aqueous solution of NADP-K at room temperature (the solution becomes turbid). After a few hours, the crystallization of β-NADP-K begins. For residual crystallization, the mixture is placed in the refrigerator ($+4°$ C.) without stirring. After 24 hours, another 30 ml of acetone is added, with brief stirring, and the mixture is let stand for 24 hours more at $+4°$ C. Then the crystallizate is suction filtered, washed in a little acetone, and vacuum dried without drying agent.

The yield amounts to about 5.4 g of β-NADP-K (90% of the theory).

EXAMPLE 3

100 ml of a 6% aqueous solution of NADP-K is treated at room temperature with about 100 ml of dioxane with stirring; the solution becomes turbid. After a few hours, the crystallization of β-NADP-K begins. For the residual crystallization, the mixture is placed in the refrigerator (+4° C.) without stirring. After 24 hours, another 30 ml of dioxane is added with brief stirring, and the mixture is let stand for another 24 hours at +4° C. Then the cristallizate is removed with a suction filter, washed in a little acetone, and dried in vacuo without drying agent.

The yield is about 5.7 g of β-NADP-K (95% of the theory).

Properties of the Product
Sum formula: $C_{21}H_{27}N_7O_{17}P_3K \cdot 2\ H_2O$
Molecular weight: β-NADP-K$\cdot 2\ H_2O = 817.5$
Melting point: 178° C. (decomposition)
NADP (determined enzymatically with ICDH): 91%
$H_2O$: 4.3%
K: 4.7%
Crystallography:
Crystal system: Primitively orthorhombic
Space Group: $P2_1 2_1 2_1$ or $P2_1 2_1 2$
Cell dimensions: $a = 52.23\ \text{Å} \pm 0.04$
  $b = 16.89\ \text{Å} \pm 0.03$
  $c = 8.45\ \text{Å} \pm 0.03$
The crystal consists of two formula units in the asymmetrical unit.

It will be understood that the specification and examples are illustrative but no limitative of the present invention and that other embodiments within the spirit and scope of the invention will suggest themselves to those skilled in the art.

What is claimed is:

1. Crystalline potassium salt of β-nicotinamide adenine dinucleotide phosphoric acid in a primitively orthorhombic crystal system, with the space group $P2_1 2_1 2_1$ or $P2_1 2_1 2$, and the cell dimensions $a = 52.23\ \text{Å} \pm 0.03$, $b = 16.89\ \text{Å} \pm 0.03$, $c = 8.45\ \text{Å} \pm 0.03$.

* * * * *